(12) United States Patent
Verardo et al.

(10) Patent No.: US 7,439,261 B2
(45) Date of Patent: Oct. 21, 2008

(54) PROCESS FOR THE PREPARATION OF VALSARTAN AND INTERMEDIATES THEREOF

(75) Inventors: Giancarlo Verardo, Pordenone (IT); Paola Geatti, Campoformido (IT); Graziano Castaldi, Briona (IT); Nicoletta Toniutti, Udine (IT); Pietro Allegrini, San Donato Milanese (IT)

(73) Assignee: Dipharma S.p.A., Mereto Di Tomba (IT)

( * ) Notice: Subject to any disclaimer, the term of this patent is extended or adjusted under 35 U.S.C. 154(b) by 588 days.

(21) Appl. No.: 10/991,431

(22) Filed: Nov. 19, 2004

(65) Prior Publication Data

US 2005/0131038 A1    Jun. 16, 2005

(30) Foreign Application Priority Data

Nov. 21, 2003    (IT)    ............ MI2003A2267

(51) Int. Cl.
*A61K 31/41* (2006.01)
*C07D 257/04* (2006.01)

(52) U.S. Cl. ...................... 514/381; 548/253
(58) Field of Classification Search ........... 514/381; 548/253

See application file for complete search history.

(56) References Cited

U.S. PATENT DOCUMENTS 5,399,578 A * 3/1995 Buhlmayer et al. ......... 514/381
6,869,970 B2 * 3/2005 Marti ........................ 514/381

* cited by examiner

*Primary Examiner*—Rei-tsang Shiao
*Assistant Examiner*—Susannah Chung
(74) *Attorney, Agent, or Firm*—Young & Thompson

(57) ABSTRACT

A novel process for the preparation of valsartan and novel intermediates useful in the preparation thereof.

10 Claims, No Drawings

PROCESS FOR THE PREPARATION OF VALSARTAN AND INTERMEDIATES THEREOF

FIELD OF THE INVENTION

The present invention relates to a novel process for the preparation of valsartan and novel intermediates useful in the preparation thereof.

TECHNOLOGICAL BACKGROUND

Valsartan, N-(1-oxopentyl)-N-[[2'-(1H-tetrazol-5-yl)[1,1'-biphenyl]-4-yl]methyl]-L-valine, is a known anti-hypertensive agent having the following formula (I):

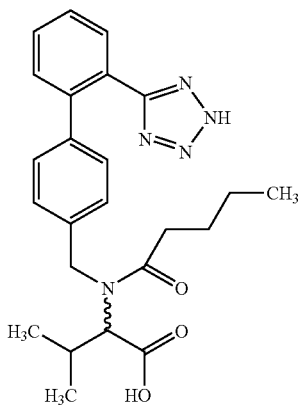

(I)

Valsartan and its preparation are disclosed in U.S. Pat. No. 5,399,578, in particular in Example 16. One of the synthetic routes according to U.S. Pat. No. 5,399,578 can be schematically represented as follows:

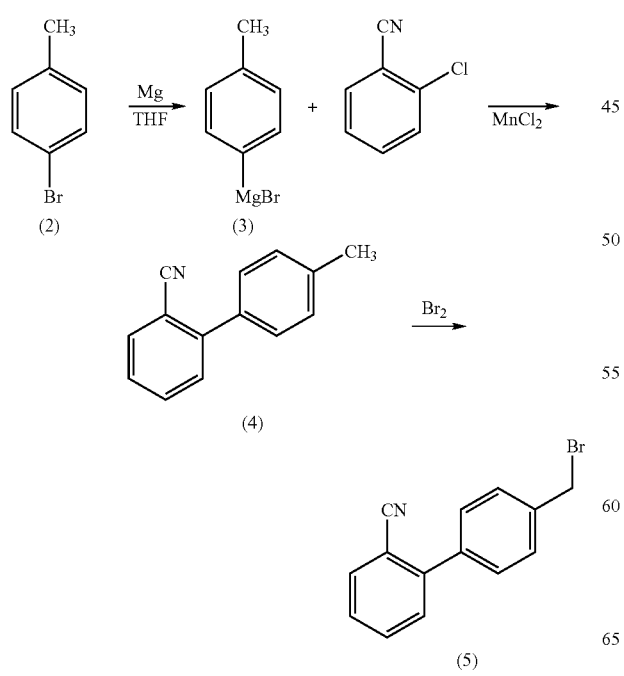

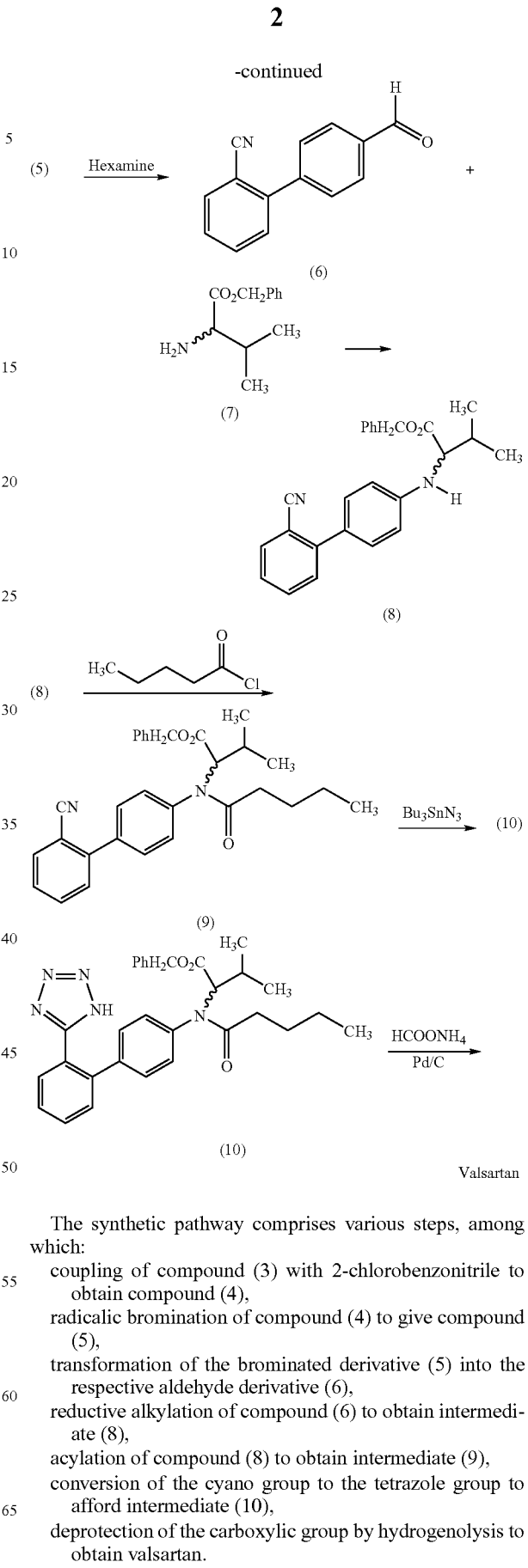

The synthetic pathway comprises various steps, among which:
- coupling of compound (3) with 2-chlorobenzonitrile to obtain compound (4),
- radicalic bromination of compound (4) to give compound (5),
- transformation of the brominated derivative (5) into the respective aldehyde derivative (6),
- reductive alkylation of compound (6) to obtain intermediate (8),
- acylation of compound (8) to obtain intermediate (9),
- conversion of the cyano group to the tetrazole group to afford intermediate (10),
- deprotection of the carboxylic group by hydrogenolysis to obtain valsartan.

The preparation of valsartan according to the scheme reported above is very complex and badly suited to the production on an industrial scale. The synthetic process involves, inter alia, the use of highly toxic compounds, such as tributyltin derivatives. It would therefore be highly desirable to provide an alternative, improved industrial process for the preparation of valsartan, which reduces costs and, preferably, avoids the conversion of the cyano group to tetrazole group in one of the last synthetic steps. This in particular would prevent the contamination of the resulting valsartan with tin or azide derivatives during the last reaction steps. Moreover, said process would be safer as the use of butyltin derivatives, which are known to be toxic, would be avoided.

It has now been found an alternative process for the preparation of valsartan which fulfils the above mentioned requirements.

DETAILED DISCLOSURE OF THE INVENTION

An object of the present invention is a novel process for the preparation of valsartan and pharmaceutically acceptable salts thereof, which comprises opening the oxazolidinone ring of a compound having formula (II),

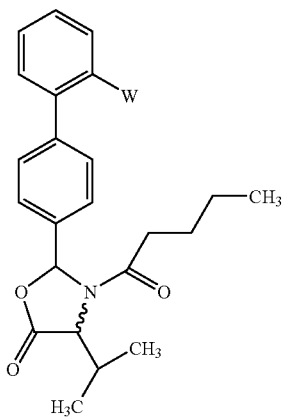

(II)

wherein W is a

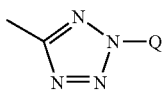

group in which Q is a protecting group; or W is a —CN group, and a) when W is a

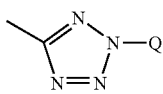

group, removing the protecting group Q; or b) when W is a —CN group, converting it to a 5-tetrazolyl group; and, if desired, converting the resulting valsartan into a pharmaceutically acceptable salt thereof.

Pharmaceutically acceptable valsartan salts are, for example, the acid or base addition salts, as disclosed in U.S. Pat. No. 6,071,931 or in WO 02/06253.

The substituent W in a compound of formula (II) is preferably a

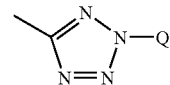

group in which Q is a protecting group.

A protecting group Q is, for example, a triphenylmethyl, tert-butyl, $C_1$-$C_4$ alkoxymethyl, methylthiomethyl, phenyl-($C_1$-$C_4$)alkoxymethyl, p-methoxybenzyl, 2,4,6-trimethylbenzyl, 1-methyl-1-phenylethyl, 2-(trimethylsilyl)ethyl, tetrahydropyranyl, piperonyl or benzenesulfonyl group; preferably a triphenylmethyl, tert-butyl or 1-methyl-1-phenylethyl group; more preferably a triphenylmethyl or 1-methyl-1-phenylethyl group.

The oxazolidinone ring of a compound of formula (II) is preferably opened through hydrogenolysis, by hydrogenation or hydrogen transfer (transfer catalysis), the latter being particularly preferred. Removal of the protecting group at the tetrazole ring may also occur during the hydrogenolysis, namely immediately before, simultaneously or immediately after the opening of the oxazolidinone ring. Hydrogenolysis through a hydrogenation reaction is carried out using molecular hydrogen in the presence of a catalyst. Hydrogenolysis by hydrogen transfer is carried out using a hydrogen donor in the presence of a catalyst. Examples of catalysts for both hydrogenolysis procedures are those selected from the group of heterogeneous catalysts, including for example Pt/C, Rh/C, Pd and Ru/C, Pd/CaCO$_3$, Pd/alumine, preferably Pd/C, in particular 5% Pd/C, or the group of the homogeneous catalysts, such as $PdCl_2(PPh_3)_2$, $Pd(OAc)_2$, $PdCl_2 \cdot PtCl_2$, $(PPh_3)_2$.

Examples of hydrogen donors are formic acid and formates in general, in particular ammonium formate; ascorbic acid; phosphinic acid, phosphinates and phosphites in general, more specifically phosphinic acid and sodium phosphinate; alcohols, such as 2-propanol, ethanol or benzyl alcohol; or hydrocarbons, such as cyclohexene, cyclohexadiene, or hydrazine, limonene, pinene or tetralin.

The reaction in both hydrogenolysis procedures can be carried out in an organic solvent for example selected from the group comprising dimethylformamide, dimethylacetamide, tetrahydrofuran, acetic acid, formic acid, dioxane, toluene, acetone and dimethylsulfoxide, preferably dimethylacetamide; at a temperature ranging approx. from room temperature to the reflux temperature of the solvent, preferably approx. from 20 to 80° C. If removal of the tetrazole protecting group does not occur during the hydrogenolysis, the removal can be carried out after the opening of the oxazolidinone ring according to known methods, for example as disclosed in WO 93/10106. When in a compound of formula (II) the substituent W is a cyano group, the intermediate resulting form the opening of the oxazolidinone ring can be isolated, if desired. The conversion of the —CN group present in this intermediate to a 5-tetrazolyl group to obtain valsartan can be carried out according to known methods, for example by reaction with HN$_3$ or a salt thereof, in particular sodium-azide or potassium-azide.

The resulting valsartan can be converted to a pharmaceutically acceptable salt as disclosed in U.S. Pat. No. 6,071,931 or in WO 02/06253.

A compound of formula (II) is novel and is a further object of the invention, together with its possible isomers.

A compound of formula (II) can be obtained by reaction of an oxazolidinone compound of formula (III)

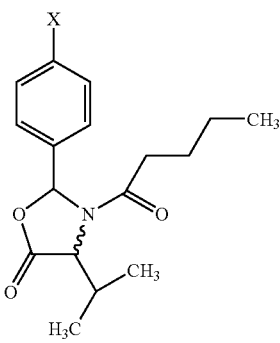
(III)

with a synthon of formula (IV)

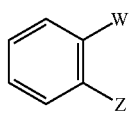
(IV)

wherein W is as defined above; and one of X and Z is a leaving group, whereas the other is a —B(R₁R₂) group wherein R₁ and R₂, which can be the same or different, are halogen, hydroxy or C₁-C₄ alkoxy; a lithium or copper atom or a halogenated metal.

A leaving group is for example a halogen atom, in particular chlorine, bromine or iodine, or a hydroxy group activated through esterification, for example with an alkanesulfonate group, typically methanesulfonyloxy, toluenesulfonyloxy, fluorosulfonyloxy, trifluoromethanesulfonyloxy or nonafluorobutanesulfonyloxy. A preferred leaving group is bromine. Examples of halogenated metals comprise —ZnCl, —MgCl, —NiCl, —CuCl, —BCl₂, —ZnBr, —MgBr, —CuBr, and —BBr₂. Synthons of formula (IV) are commercially available. The preparation of a compound of formula (IV), as well as the reaction between a compound of formula (III) and a compound of formula (IV), can be carried out according to known methods, such as those disclosed in EP 579 766, EP 539 086, EP 760 815, WO 93/10106 or EP 782 996.

Alternatively, a compound of formula (II) can also be obtained by reacting a compound of formula (V)

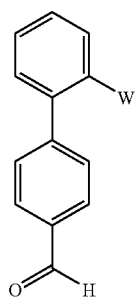
(V)

wherein W is as defined above, with L-valine or a reactive derivative thereof, such as an ammonium or alkali salt thereof, preferably sodium, or a tri(alkyl)-silyl ester thereof, for example a tri(C₁-C₆ alkyl)silyl ester, and subsequently reacting with valeryl chloride according to known methods. A compound of formula (V) in which W is a —CN group is known for example from U.S. Pat. No. 5,399,578 and, if desired, can be converted to another compound of formula (V) in which W is a

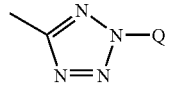

group wherein Q is as defined above, according to known methods, for example as disclosed in U.S. Pat. No. 5,399,578.

According to a preferred embodiment of the invention, a compound of formula (II) is obtained by reacting a compound of formula (III) with a compound of formula (IV) in which W is a

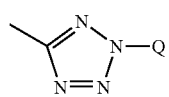

group wherein Q is as defined above.

A compound of formula (III) is novel and is a further object of the invention, together with its possible isomers. It can be obtained by reaction of an imine of formula (VI)

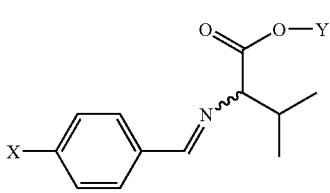
(VI)

wherein X is as defined above and Y is a cation, for example a metal, preferably an alkali metal such as sodium or potassium or an ammonium group, preferably trimethylbenzyl ammonium; or a tri(alkyl)silyl group, in particular tri(C₁-C₆ alkyl)silyl, with valeryl chloride (nBuCOCl), according to known methods, (Helv. Chim. Acta, 68, 1985, 1245). A compound of formula (VI) can be obtained by reacting known benzaldehyde derivatives substituted at the para position with an X group, as defined above, with L-valine or an alkali salt thereof, preferably sodium, or an ammonium salt or ester thereof, according to known methods.

The process according to the invention for the preparation of valsartan substantially includes the following 4 steps:
preparation of imine (VI);
acylation of compound (IV) to obtain the oxazolidinone derivative (III);
coupling to give compound (II); and
opening of the oxazolidinone ring of compound (II) to obtain valsartan;
or:
preparation of aldehyde (V);

reaction of compound (V) with L-valine or a reactive derivative thereof;

subsequent acylation to obtain compound (II); and opening of the oxazolidinone ring of compound (II) to obtain valsartan.

The novel process herein described provides evident operational advantages, in that it requires less reaction steps and makes use of commercially available, non toxic compounds. In particular, when hydrogenolysis of a compound of formula (II) is carried out under transfer catalysis, evident advantages are obtained in terms of both safety, as the use of flammable hydrogen is avoided, and plants, as no pressurized reactors are necessary.

It should also be noticed that the tetrazole ring in the synthon of formula (IV) can be prepared separately and used in one of the starting steps of the process. Analogously, the intermediates containing a cyano group can be converted to the corresponding intermediates containing a 5-tetrazolyl group in the first synthetic steps, thereby reducing the possibility of contaminating the resulting valsartan with tin or azide derivatives. Valsartan obtained by the process of the invention is in fact substantially pure, and in particular substantially free from tin or azide derivatives. The expression "substantially pure" means having a purity degree equal to or higher than 99%. The expression "substantially free from tin or azide derivatives" means having a content in said contaminants equal to or lower than 20 ppm.

The following examples further illustrate the invention.

The $^1$H-NMR and $^{13}$C-NMR spectra were recorded with a Bruker 200 MHz apparatus.

EXAMPLE 1

2-[(4-Bromobenzylidene)amino]-3-methylbutyric acid sodium salt; (intermediate VI)

2.0 g of NaOH powder (49.5 mmoles) and L-valine 6.5 g (55.5 mmoles) are reacted in 50 ml of dry methanol. After stirring for 10 minutes at 25° C., 7.8 g of 4-bromobenzaldehyde (42.2 mmoles) are added to the mixture, which is left under stirring for 1 hour. The solution is filtered and concentrated at 40° C. under reduced pressure to obtain a solid or oily residue. The sample is kept at 50° C. under reduced pressure for 3 hours, to remove the water formed during the reaction, thereby obtaining 2-[(4-bromobenzylidene)amino]-3-methylbutyric acid sodium salt as a solid (12.6 g, 41.1 mmoles; molar yield: 97%).

$^1$H-NMR (CH$_3$OD): δ (ppm): 0.85 (d, 3H), 0.96 (d, 3H); 1.95-2.15 (m, 0.15 H), 2.20-2.40 (m, 0.85 H); 3.15 (d, 0.15 H); 3.45 (d, 0.85 H); 7.58 (d, 2H); 7.69 (d, 2H); 8.20 (s, 1H).

EXAMPLE 2

2-(4-Bromophenyl)-4-isopropyl-3-pentanoyl-oxazolidin-5-one; (intermediate (III))

12.6 g of 2-[(4-bromobenzylidene)amino]-3-methylbutyric acid sodium salt (41.1 mmoles) are suspended in 80 ml of dry dichloromethane. The mixture is refluxed (40° C.), under slight nitrogen stream. 7.9 g of valeryl chloride (65.5 mmoles) are added. After 2 hours under reflux, the mixture is cooled to 25° C. The organic phase is washed three times with 50 ml of water and concentrated under reduced pressure, at 25-30° C., to obtain an oily residue. 50 ml of ethyl acetate are added and the organic phase is washed with a weakly basic NaOH solution and/or with water to neutrality. The organic phase is washed with a sodium bisulfite solution. The organic phase is washed with water and dried over sodium sulfate, filtered and evaporated under reduced pressure. The oily residue is taken up with ethanol from which the product crystallizes as a white solid. 2-(4-Bromophenyl)-4-isopropyl-3-pentanoyl-oxazolidin-5-one is obtained (5.2 g; 14.1 mmoles; molar yield: 34%).

$^1$H-NMR (CDCl$_3$): δ 0.60-1.35 (m, 11H); 1.4 (m, 2H); 1.80-2.0 (m, 0.5H); 2.20-2.40 (m, 1H), 2.80-3.00 (m, 0.5H), 4.50 (s, 0.4 H), 4.7 (s, 0.6 H), 6.4 (s, 1H), 7.20 (d, 2H); 7.50 (dd, 2H).

EXAMPLE 3

4-Isopropyl-3-pentanoyl-2-[2'-(1-trityl-1H-tetrazol-5-yl)-biphenyl-4-yl]oxazolidin-5-one (intermediate (II))

Preparation of the catalyst: 131 mg of triphenylphosphine (0.50 mmoles) are dissolved in 10 ml of anhydrous THF. 28 mg of Pd(OAc)$_2$ (palladium acetate) (0.12 mmoles) are added and the mixture is kept at 60° C. for 30 min, then cooled to 25° C.

Reaction: 5.75 g (13.3 mmoles) of 2-(2'-triphenylmethyl-2'H-tetrazol-5'-yl)-phenylboronic acid are mixed with 33 g of diethoxymethane and 0.28 g of water. The mixture is stirred for 30 min at 25° C., then added with 4.3 g of potassium carbonate (31.1 mmoles), 0.28 g of water and 4.6 g (12.5 mmoles) of 2-(4-bromophenyl)-4-isopropyl-3-pentanoyl-oxazolidin-5-one (intermediate (III)). The mixture is kept at 25° C. for 30 min, then the catalyst solution is added thereto, heating at 79° C. for 2-6 hours. After completion of the reaction, the mixture is diluted with water and diethoxymethane, the organic phase is separated and the solvent is evaporated off under reduced pressure, thereby obtaining an oil, which contains 6.7 g (10.0 mmoles) of product (molar yield: 80%).

$^1$H-NMR (DMSO) (0.7 (t, 3H); 0.75-0.95 (m, 3H); 1.00-1.25 (m, 4.6 H), 1.95-2.10 (m, 1.4H); 2.25-2.40 (m, 1.4 H); 2.65-2.80 (m, 0.6 H); 4.83 (s, 0.7 H); 4.98 (s, 0.3 H); 6.65 (s, 0.3 H); 7.00 (s, 0.7 H); 7.00-7.90 (m, 23 H).

EXAMPLE 4

Valsartan 1.0 g (1.5 mmoles) of 4-isopropyl-3-pentanoyl-2-[2'-(1-trityl-1H-tetrazol-5-yl)-biphenyl-4-yl]oxazolidin-5-one are reacted in 50 ml of N,N,-dimethyl-acetamide with 1.2 g of ammonium formate (19.0 mmoles) and 1.2 g of 5% Pd/C catalyst. The temperature is raised to 90° C. and ammonium formate is added in 1.2 g (19.0 mmoles) portions, at 2 hours interval, until disappearance of the starting substrate. The mixture is cooled and the catalyst is filtered off. tert-Butyl methyl ether and 20% sulfuric acid are added to about pH 2, then sodium chloride to saturation of the aqueous phase. The organic phase is separated and washed with water 3 times. The organic phase is alkalinised with a 10% sodium hydroxide solution. The aqueous phase containing the salified product is separated and washed with tert-butyl methyl ether. Ethyl acetate is added and acidified with a 5% hydrochloric acid solution. The organic phase is separated, dried over sodium sulfate, filtered and concentrated under reduced pressure to a residue. Crystallization from isopropyl ether affords 0.44 g of valsartan (1.05 mmoles; yield: 70%), having purity higher than 99.5% and content in azide derivatives lower than 20 ppm.

$^1$H-NMR (CDCl$_3$) (0.80-1.15 (m, 9H); 1.20-1.50 (m, 2H); 1.60-1.80 (m, 2H); 2.60 (t, 2H); 2.65-2.80 (m, 2H), 3.70 (d, 1H), 4.10 (d, 0.3 H), 4.30 (d, 0.7 H), 4.90 (d, 0.7H), 5.2 (d, 0.3H); 7.00 (d, 0.3H); 7.10-7.20 (m, 4H), 7.40-7.60 (m, 3H), 7.85 (d, 0.7 H).

EXAMPLE 5

Valsartan

A solution of the 4-isopropyl-3-pentanoyl-2-[2'-(1-trityl-1H-tetrazol-5-yl)-biphenyl-4-yl]oxazolidin-5-one (1.0 g, 1.5 mmoles) in 20 ml of THF is hydrogenated under 5 bars, at 60° C., in the presence of Pd(5%)/C (100 mg). After completion of the reaction, the mixture is cooled and the catalyst is filtered off. After working up the reaction mixture as in Example 4, valsartan (0.33 g, molar yield: 53%) is isolated by crystallization from isopropyl ether.

EXAMPLE 6

4'-(4-Isopropyl-5-oxo-3-pentanoyl-oxazolidin-2-yl) biphenyl-2-carbonitrile; (intermediate (II))

2.0 g of NaOH powder (49.5 mmoles) and L-valine 6.5 g (55.5 mmoles) are reacted in 50 ml of dry methanol. The mixture is stirred at 25° C. for 10 minutes, then evaporated in rotary evaporator, added with 8.7 g (42.2 mmoles) of 4'-formyl biphenyl-2-carbonitrile and 50 ml of isopropanol and left under stirring for 1 hour. The solution is concentrated at 60° C. under reduced pressure to obtain a solid or oily residue, which is kept at 50° C. under reduced pressure for 3 hours to remove the water formed during the reaction. A solid is obtained in molar yield equivalent to 90% (12 g, 38.0 mmoles). The solid is suspended in 80 ml of dry dichloromethane and heated to reflux under mild nitrogen stream. 2.1 g of triethylamine (20.8 mmoles) and 7.9 g of valeryl chloride (65.7 mmoles) are added to the mixture, that is refluxed for 2 hours, then cooled to 25° C. The organic phase is washed three times with 50 ml of water and concentrated under reduced pressure at 25-30° C., to obtain an oily residue. 50 ml of ethyl acetate are added and the organic phase is washed with a weakly basic NaOH solution, then with water to neutrality. The organic phase is washed with a sodium bisulfite solution, then with water, dried over sodium sulfate, filtered and evaporated under reduced pressure. The oily residue is taken up with isopropanol from which the title product crystallizes (8.2 g, 21.1 mmoles; molar yield: 50%).

$^1$H-NMR (CDCl$_3$) (0.60-1.35 (m, 11H); 1.4 (m, 2H); 1.80-2.0 (m, 0.5H); 2.20-2.40 (m, 1H), 2.80-3.00 (m, 0.5H), 4.50 (s, 0.4 H), 4.7 (s, 0.6 H), 6.5 (s, 1H), 7.3 (d, 2H); 7.54 (dd, 2H).

EXAMPLE 7

2-[(2'-Cyano-biphenyl-4-yl methyl)-pentanoyl-amino]-3-methylbutyric acid 6.0 g (15.4 mmoles) of 4'-(4-isopropyl-5-oxo-3-pentanoyl-oxazolidin-2-yl)-biphenyl-2-carbonitrile is reacted in 30 ml of ethanol with 3.8 g of ammonium formate (61.6 mmoles) and 2 g of 5% Pd/C catalyst. The temperature is raised to 75° C., keeping these conditions for 3 hours. The mixture is cooled and the catalyst is filtered off. The organic phase is concentrated under reduced pressure to a residue to obtain 2-[(2'-cyano-biphenyl-4-yl-methyl)-pentanoyl-amino]-3-methylbutyric acid.

$^1$H-NMR (CDCl$_3$) (0.80-1.15 (m, 9H); 1.20-1.50 (m, 2H); 1.60-1.80 (m, 2H); 2.40-2.55 (m, 2H), 2.60-2.80 (m, 1H); 3.80 (d, 0.7 H), 3.90 (d, 0.3 H); 4.45 (d, 0.7 H), 4.50 (d, 0.3 H), 4.82 (d, 0.7H), 4.85 (d, 0.3H); 7.10-7.20 (m, 4H), 7.40-7.70 (m, 4H).

The invention claim is:

1. A process for the preparation of valsartan, or a pharmaceutically acceptable salt thereof, comprising:

opening the oxazolidinone ring in a compound having formula (II),

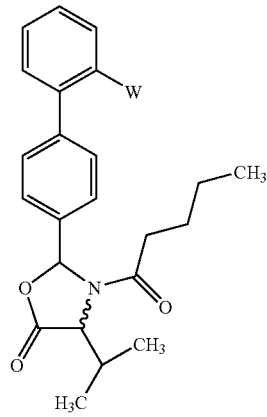

(II)

wherein W is one of a

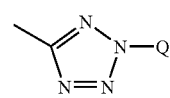

group in which Q is a protecting group and a —CN group, and
a) when W is a

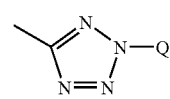

group, removing the protecting group Q immediately before, simultaneously, or immediately after the opening of the oxazolidinone ring and b) when W is a —CN group, converting the —CN group to a 5-tetrazolyl group through hydrogenolysis, by one of hydrogenation reaction in the presence of a catalyst and hydrogen transfer reaction in the presence of a catalyst and a hydrogen donor; and optionally transforming the resulting valsartan into a pharmaceutically acceptable salt.

2. A process according to claim 1, wherein the protecting group Q is selected from triphenylmethyl, tert-butyl, $C_1$-$C_4$ alkoxymethyl, methylthiomethyl, phenyl-($C_1$-$C_4$) alkoxymethyl, p-methoxybenzyl, 2,4,6-trimethylbenzyl, 1-methyl-1-phenylethyl, 2-(trimethylsilyl)ethyl, tetrahydropyranyl, piperonyl and benzenesulfonyl.

3. A process according to claim 1, wherein, the oxazolidinone ring is opened through hydrogenolysis by hydrogenation reaction in the presence of a catalyst, and the catalyst is one of (i) a heterogeneous catalyst selected from the group consisting of Pt/C, Rh/C, Pd, Ru/C, Pd/CaCO$_3$, and Pd/alumine and (ii) a homogeneous catalyst selected from the group consisting of PdCl$_2$(PPh$_3$)$_2$, Pd(OAc)$_2$, PdCl$_2$, and PtCl$_2$(PPh$_3$)$_2$.

4. A process according to claim 1, wherein, the oxazolidinone ring is opened through hydrogenolysis by hydrogen transfer reaction in the presence of a catalyst and a hydrogen donor, and the catalyst is one of (i) a heterogeneous catalyst selected from the group consisting of Pt/C, Rh/C, Pd, Ru/C, Pd/CaCO$_3$, and Pd/alumine and (ii) a homogeneous catalyst selected from the group consisting of PdCl$_2$(PPh$_3$)$_2$, Pd(OAc)$_2$, PdCl$_2$, and PtCl$_2$(PPh3)$_2$.

5. A process according to claim 4, wherein the catalyst is Pd/C.

6. A process according to claim 4, wherein the hydrogen donor is selected from formic acid, ammonium formate, ascorbic acid, phosphinic acid, sodium phosphinate, 2-propanol, ethanol, benzyl alcohol, cyclohexene; cyclohexadiene, hydrazine, limonene, pinene and tetralin.

7. A process according to claim 6, wherein the hydrogen donor is ammonium formate.

8. A process according to claim 1, wherein in a compound of formula (II) W is a

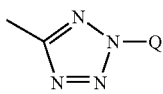

group in which Q is a protecting group.

9. A compound having formula (II),

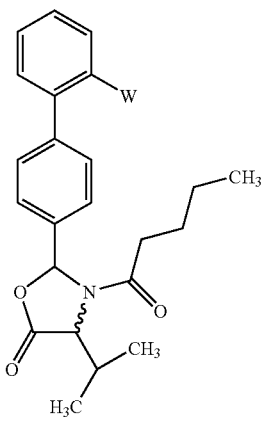

(II)

wherein W is a

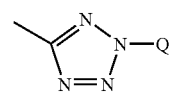

group in which Q is a protecting group; or W is a —CN group.

10. A compound of formula (III),

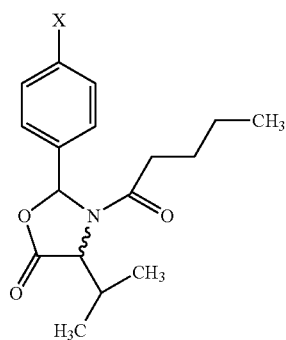

(III)

wherein X is a leaving group; a —B (R$_1$R$_2$) group wherein R$_1$ and R$_2$, which can be the same or different, are halogen, hydroxy or C$_{1-4}$ alkoxy; a lithium or copper atom or a halogenated metal.

* * * * *